US006835566B2

(12) United States Patent
Smith et al.

(10) Patent No.: US 6,835,566 B2
(45) Date of Patent: Dec. 28, 2004

(54) HUMAN LINEAGE COMMITTED CELL COMPOSITION WITH ENHANCED PROLIFERATIVE POTENTIAL, BIOLOGICAL EFFECTOR FUNCTION, OR BOTH; METHODS FOR OBTAINING SAME; AND THEIR USES

(75) Inventors: Alan K. Smith, Saline, MI (US); Douglas M. Smith, Ann Arbor, MI (US); Ramkumar K. Mandalam, Westland, MI (US)

(73) Assignee: Aastrom Biosciences, Inc., Ann Arbor, MI (US)

( * ) Notice: Subject to any disclaimer, the term of this patent is extended or adjusted under 35 U.S.C. 154(b) by 149 days.

(21) Appl. No.: 09/893,470

(22) Filed: Jun. 29, 2001

(65) Prior Publication Data

US 2002/0031498 A1 Mar. 14, 2002

Related U.S. Application Data

(63) Continuation of application No. 09/027,671, filed on Feb. 23, 1998.

(51) Int. Cl.$^7$ ................................................ C12N 5/06
(52) U.S. Cl. ........................... 435/355; 435/2; 435/371; 435/372; 435/372.1; 435/377; 435/400; 435/401
(58) Field of Search ........................... 435/2, 355, 371, 435/372, 372.1, 377, 400, 401

(56) References Cited

U.S. PATENT DOCUMENTS

| | | | |
|---|---|---|---|
| 4,135,975 A | 1/1979 | Lichtman et al. | |
| 4,481,946 A | 11/1984 | Altshuler et al. | |
| 4,486,188 A | 12/1984 | Altshuler et al. | |
| 4,514,499 A | 4/1985 | Noll | |
| 4,714,680 A | 12/1987 | Civin | |
| 4,808,611 A | 2/1989 | Cosman | |
| 4,810,643 A | 3/1989 | Souza | |
| 4,847,201 A | 7/1989 | Kaswasaki et al. | |
| 4,861,714 A | 8/1989 | Dean et al. | |
| 4,889,812 A | 12/1989 | Guinn et al. | |
| 4,963,489 A | 10/1990 | Naughton et al. | |
| 4,965,204 A | 10/1990 | Civin | |
| 5,004,681 A | 4/1991 | Boyse et al. | 435/2 |
| 5,032,407 A | 7/1991 | Wagner et al. | |
| 5,032,508 A | 7/1991 | Naughton et al. | |
| 5,061,620 A | 10/1991 | Tsukamoto et al. | |
| 5,199,942 A | 4/1993 | Gillis | |
| 5,399,493 A | 3/1995 | Emerson et al. | |
| 5,605,822 A | 2/1997 | Emerson et al. | |
| 5,635,386 A | 6/1997 | Palsson et al. | |
| 5,646,043 A | 7/1997 | Emerson et al. | |
| 5,670,147 A | 9/1997 | Emerson et al. | |
| 5,670,351 A | 9/1997 | Emerson et al. | |
| 5,674,750 A | * 10/1997 | Kraus et al. | 435/372 |
| 5,728,581 A | * 3/1998 | Schwartz et al. | 435/385 |
| 5,811,094 A | 9/1998 | Caplan et al. | |
| 5,851,832 A | 12/1998 | Weiss et al. | |
| 5,922,597 A | 7/1999 | Verfaillie et al. | |
| 5,925,567 A | 7/1999 | Kraus et al. | 435/372 |
| 5,945,225 A | 8/1999 | Speith-Herfurth et al. | |
| 5,994,126 A | * 11/1999 | Steinman et al. | 435/325 |
| 6,299,650 B1 | 10/2001 | Van Blitterswijk et al. | |
| 6,326,198 B1 | 12/2001 | Emerson et al. | |

FOREIGN PATENT DOCUMENTS

| | | |
|---|---|---|
| EP | 0 358 506 | 3/1990 |
| EP | 0 455 482 | 11/1991 |
| WO | 90/15877 A2 | 12/1990 |
| WO | 93/18136 | 9/1993 |
| WO | 93/18137 | 9/1993 |
| WO | 95/06409 | 3/1995 |

OTHER PUBLICATIONS

Romani et al, Jour. Exper. Med., 180, 83–93, 1994.*
Siena et al, Exper. Hematol., 23, 1463–1471, 1995.*
M. W. Glacken et al., "Mammalian cell culture: engineering principles and scale–up", Trends in Biotechnology, vol. 1, No. 4, 1983, pp. 102–108.
Steven A. Rosenberg et al., "In Vitro Growth of Murine T Cells II. Growth of In Vitro Sensitized Cells Cytotoxic for Alloantigens", The Journal of Immunology, vol. 121, No. 5. Nov. 1978, pp. 1951–1955.
W. French Anderson, "Prospects for Human Gene Therapy", Science, vol. 26, Oct. 26, 1987, pp. 401–409.
T.M. Dexter, "The Message in the medium", Nature, vol. 309, Jun. 1984, pp 746–747.
Manfred R. Koller, et al. "Expansion of Primitive Human Hematopoietic Progenitors in a Perfusion Bioreactor System with LL–3, LL–6, and Stem Cell Factor", Biotechnology, vol. 11, Mar., 1993, pp. 358–363.
Bernhard O. Palsson et al, "Expansion of Human Bone Marrow Progenitor Cells in a High Cell Density Continuous Perfusion System", Biotechnology, vol. 11, Mar., 1993, pp. 368–372.
Giovanni Migliaccio et al., "In Vitro Differentiation of Human Granulocyte/Macrophage and Erythroid Progenitors: Comparative Analysis of the Influence of Recombinant Human Erythropoietin, G–CSF, GM–CSF, and IL–3 in Serum–Supplemented and Serum–Deprived Cultures", Blood, vol. 72, No. 1 Jul. 1988, pp. 248–255.
Ian K. McNiece et al., "Studies on the Myeloid Synergistic Factor From 5637:Comparison with Interleukin–1 Alpha", Blood, vol. 73, No. 4 (Mar.), 1989, pp. 919–923.

(List continued on next page.)

*Primary Examiner*—David Saunders
(74) *Attorney, Agent, or Firm*—Oblon, Spivak, McClelland, Maier & Neustadt, P.C.

(57) ABSTRACT

A method for obtaining lineage committed human cells imbued with enhanced proliferative potential, biological function, or both, comprising culturing lineage committed human cells under physiologically acceptable liquid culture conditions, where the liquid culture medium is replaced at a rate and for a time sufficient to obtain the human lineage committed cells imbued with enhanced proliferative potential, biological function, or both; and isolating the cultured cells.

18 Claims, 6 Drawing Sheets

Paul Baines et al., Exp. Hematol. 16:785–789 (1988).
Jan A. Nolta et al., Human Gene Therapy, 1:257–268 (1990).
John R. Stephenson et al., Proc. Nat. Acad. Sci. U.S.A., vol. 68, No. 7, pp. 1542–1546, Jul. 1971.
Giovanni Migliaccio et al., Exp. Hematol. 18:1049–1055 (1990).
Richard M. Schwartz et al., "In Vitro Myelopoiesis Stimulated by Rapid Medium Exchange and Supplementation With Hematopoietic Growth Factors", Blood, vol. 78, No. 12, Dec. 15, 1991, pp. 3155–3161.
Rob E. Ploemacher et al., "Use of Limiting–Dilution Type Long–Term marrow cultures in frequency amalysis of Marrow–Repopulating and Spleen Colony–Forming Hematopoietic Stem Cells in the Mouse", Blood, vol. 78, No. 10 (Nov. 15, 1991, pp. 2527–2533.
Manfred R. Koller et al., "Effect of Synergistic Cytokine Combinations, Low Oxygen, and Irradiated Stroma on the Expansion of Human Cord Blood Progenitors", Blood, vol. 80, No. 2 (Jul. 15, 1992), pp. 403–411.
J. Aiken et al., Journal of Pediatric Surgery, vol. 25, No. 1 (Jan.), 1990; pp. 140–145.
C. Favre et al., "Interleukin–4 has Basophilic and Eosinophilic Cell Growth–Promoting Activity on Cord Blood Cells", Blood, vol. 1, Jan. 1, 1990, pp. 67–73.
Yoichi Takaue et al., "Limiting–Dilution Analysis of the Effects of Colony–Stimulating Factors, Phytohemagglutinin, and Hydrocortisone on Hematopoietic Progenitor Cell Growth", Blood, vol. 70, No. 5, Nov., 1987, pp. 1611–1618.
Yoichi Takaue et al., "Effect of Recombinant Human G–CSF, GM–CSF, IL–3, and IL–1α on the Growth of Purified Human Peripheral Blood Progenitors", Blood, vol. 76, No. 2, Jul. 15, 1990, pp. 330–335.
H. J. Sutherland et al., "Alternative Mechanisms With and Without Steel Factor Support Primitive Human Hematopolesis", Blood, vol. 81, No. 6., Mar. 15, 1993, pp. 1465–1470.
Lucia H. Coulinho et al., "Effects of Recombinant Human Granulocyte Colony–Stimulating Factor (CSF), Human Granulocyte Macrophage–CSF, and Gibbon Interleukin–3 on Hematopoiesis in Human Long–Term Bone Marrow Culture", Blood, vol. 11, Jun. 1, 1990, pp. 2118–2129.
Susan C. Guba et al., "Bone Marrow Stromal Fibroblasts Secrete Interleukin–6 and Granulocyte–Macrophage Colony–Stimulating Factor in the Absence of Inflammatory Stimulation: Demonstration by Serum–Free Bioassay, Enzyme–Linked Immunosorbent Assay, and Reverse Transcriptase Polymerase Chain Reaction", Blood, vol. 80, No. 5, Sep. 1, 1992, pp. 1190–1198.
Richard M. Schwartz et al., "Rapid medium perfusion rate significantly increases the productivity and longevity of human bone marrow cultures", Proc. Natl. Acad. Sci. USA, vol. 88, pp. 6760–6764, Aug. 1991.
David E. Harrison et al., "Primitive hemopoietic stem cells: direct assay of most productive populations by competitive repopulation with simple binomial, correlation and covarlance calculations", Experimental Hematology 21:206–219 (1993).
D. Krumwieh et al., "Preclinical Studies on Synergistic Effects of IL–1, IL–3, G–CSF and GM–CSF in Cynomoigus Monkeys", International Journal of Cell Cloning 8:229–248, Suppl. 1 (1990).
Makio Ogawa, Ph.D., "Effects of Hemopoietic Growth Factors on Stem Cells In Vitro", Hematology/Oncology Clinics of North America, vol. 3(3) Sep. 1989, pp. 453–464.

Jerry Caldwell et al., "Culture Perfusion Schedules Influence the Metabolic Activity and Granulocyte–Macrophage Colony–Stimulating Factor Production Rates of Human Bone Marrow Stromal Cells"., Journal of Cellular Physiology, 147:344–353 (1991).
C.M. Heyworth et al., "The Role of Hemopoietic Growth Factors in Self–Renewal and Differentiation of IL–3 Dependent Multipotential Stem Cells"., Growth Factors, 1990, vol. 2, pp. 197–211.
Shiang Huang et al., "Formation of haematopoietic Microenvironmental and haematopoietic stem cells from single human bone marrow stem cells", Nature, vol. 360, Dec. 24/31, 1992, pp. 745–749.
Randy A. Hock et al., "Retrovirus–mediated transfer and expression of drug resistance genes in human haematopoietic progenitor cells", Nature, vol. 320, Mar. 1986, pp. 275–277.
A.A. Fauser et al., "Granuloerythropoietic Colonies In Human Bone Marrow. Peripheral Blood, and Cord Blood" Blood, vol. 52, No. 6, Dec. 1978, pp. 1243–1248.
C.D. Myers et al., "A Cell Line Secreting Stimulating Factors for CFU–GEMM Culture", Blood, vol. 64, No. 1 (Jul.) 1984, pp. 152–155.
Alice M. Wang et al., "Molecular Cloning of the Complementary DNA for Human Tumor Necrosis Factor", Science, vol. 228, Noc. 20, 1984, pp. 149–154.
Colin A. Sieff et al., "Human Recombinant Granulocyte–Macrophage Colony–Stimulating Factor: A Multilineage Hematopoietin" Science, vol. 230, Dec. 6, 1985, pp. 1171–1173.
Robert E. Donahute et al., "Human IL–3 and GM–CSF Aci Synergistically in Stimulating Hematopoiesis In Primates", Science, vol. 241, Sep. 30, 1988, pp. 1820–1823.
Ronald H. Schwartz, "A Cell Culture Model for T Lymphocyte Clonal Anergy", Science, vol. 248, Jun. 15, 1990, pp. 1349–1356.
Toshio Suda et al., "A Stimulatory Effect of Recombinant Murine Interleukin–7 (IL–7) on B–Cell Colony Formation and an Inhibitory Effect of IL–1α", Blood, vol. 74, No. 6, Nov. 1, 1989, pp. 1936–1941.
Heather J. Sutherland et al., "Characterization and Partial Purification of Human Marrow Cells Capable on Initiating Long–Term Hematopoiesis In Vitro", Blood, vol. 74, No. 5 (Oct.) 1989; pp. 1563–1570.
Sem Seeland et al., "Combined and Sequential Effects of Human IL–3 and GM–CSF on the Proliferation of CD34+ Hematopoietic Cells From Cord Blood"., Blood, vol. 73, No. 5, (Apr.), 1989; pp. 1195–1201.
Sallie S, Boggs, "Targeted Gene Modification for Gene Therapy of Stem Cells", International Journal of Cell Cloning 8:80–96 (1990).
Cynthia E. Dunbar et al., "Gene Transfer Into Hematopoietic Progenitor and Stem Cells: Progress and Problems", Stem Cells 1994;12:563–576.
Angelika Mueller, "Die Knochenmarkstammzellkultur Technische Voraussetzungen und klinische Einsatzmoeglichkelten", Folia Haematol., Leipzig 116 (1989) 5, 731–743.
Stephen G. Emerson et al., "Purification of Fetal Hematopoietic Progenitors and Demonstration of Recombinant Multipotential Colony–stimulating Activity", The Journal of Clinical Investigation, vol. 76, Sep. 1985, 1286–1290.
Pp. 573–578: "Clinical Transplantation", In *Immunology*, Second Edition, J. Kuby, W.H. Freeman and Company, New York (1994).

Theodore Friedmann, "Overcoming the Obstacles–Treating disease by providing needed genes remains a compelling idea, but clinical and basic researchers still have much to do before gene therapy can live up to its promise",Scientific American, Jun. 1997, pp. 96–101.

Joseph Feder et al., "The Large–Scale Cultivation of Mammalian Cells", Scientific American, vol. 248, No. 1 (Jan. 1983), pp. 24–31.

Heather J. Sutherland, "Functional characterization of individual human hematopoietic stem cells cultured at limiting dilution on supportive marrow stromal layers", Proc. Natl. Acad. Sci. USA, vol. 87 (1990), pp. 3584–3588.

Janice L. Gabrilove et al., "Pluripoletin α: A second human hematopoietic colony–stimulating factor produced by the human bladder carcinoma cell line 5637", Proc. Natl. Acad. Sci. USA, vol. 83, pp. 2478–2482, Apr. 1986.

Jeffrey A. Hubbell et al., Endothelial Cell–Selective Materials for Tissue Engineering in the Vascular Graft Via a New Receptor, Biotechnology, vol. 9, Jun. 1991, pp. 568–572.

Jerry Caldwell et al., "Influence of Medium Exchange Schedules on Metabolic, Growth, and GM–CSF Secretion Rates of Genetically Engineered NlHo–3T3 Cells", Biotechnology Progress, vol. 7, No. 1, Jan./Feb. 1991, pp. 1–8.

Li Lu et al., "Effect of recombinant and purified human haematopoietic growth factors on in vitro colony formation by enriched populations of human megakaryocyte progenitor cells", British Journal of Haematology, 1988, vol. 70, pp. 149–156.

A. Montes Borinaga et al., "Interleukin–6 is a cofactor for the growth of myeloid cells from human bone marrow aspirates but does not affect the clonogenecity of myeloma cells in vitro", British Journal of Haematology, 1990, No. 76, pp. 476–483.

P.M. Lehn., "Gene therapy using bone marrow transplantation: a 1990 update", Bone Marrow Transplantation (1990), No. 5, pp. 287–293.

Manfred R. Koller et al., "Beneficial Effects of Reduced Oxygen Tension and Perfusion in Long–Term Hematopoietic Cultures", Biochemical Engineering, VII. vol. 665 of the Annals New York Academy of Sciences, pp. 105–116, (Oct. 1992).

D. Krumwieh et al., "Human Recombinant Derived IL–3 and GM–CSF in Hematopoietic of Normal Cynomoigus Monkeys", Behring Inst., Mitt., No. 83, pp. 250–257 (1988).

John Brandt et al., "Detection of Human Hematopoietic Progenitor Cell Capable of Forming Blast Cell Containing Colonies In Vitro", Advances in Experimental Medicine and Biology, vol. 241, pp. 165–173.

C.J. Eaves et al., "The Human Hematopoietic Stem Cell In Vitro and In Vivo", Blood Cells (1992) 18:301–307.

Masaaki Ishizuka et al., "Milogenic Effect of Bestalin on Lymphocytes", The Journal of Antibiotics, vol. 33, No. 6, (Jun. 1980), pp. 653–662.

Donald B. Kohn Ph.D. et al., "Gene Therapy for Genetic Diseases", Cancer Investigation, 7(2), pp. 179–192 (1989).

Maria Podolak–Dawidziak et al., "Does Human Bladder Carcinoma Cell Line 5637–Conditioned Medium Supplement the Growth of Megakaryocyte Colonies (CFU–Mk) in Cultures of Human bone Marrow", Haematologia, 23:121–123.

Jan A. Nolta et al., "Comparison of the Effects of Growth Factors on Retroviral Vecto–Mediated Gene Transfer and the Proliferative Status of Human Hematopoietic Progenitor Cells", Human Gene Therapy, 1:257–268 (1990).

Christoph Heberlein et al., "The Gene for Erythropoietin Receptor is Expressed in Multipotential Hematopoietic and Embryonal Stem Cells: Evidence for Differentiation Stage–Specific Regulation", Molecular and Cellular Biology, vol. 12 (14) pp. 1815–1826, (1992).

Nicholas Dainlak et al., "Interactions of Insulin, Insulinlike Growth Factor II, and Platelet–derived Growth Factor in Erythropoietic Culture", J. Clin. Invest. vol. 76, Sep. 1985, 1237–1242.

Yves–Jacques Schneider et al., "Monoclonal Antibody Production in Semi–Continuous Serum–and protein–free culture", Journal of Immunological Methods, vol. 129 (1990) pp. 251–268.

Philip W. Kantoff et al., "Expression of Human Adenosine Deaminase in Nonhuman Primates after Retrovirus–Mediated Gene Transfer", J. Exp. Med. vol. 166, Jul. 1987, pp. 219–234.

Suzanne Gartner et al., "Long–term culture of human bone marrow cells", Proc. Natl. Acad. Sci. USA, vol. 77, No. 8, pp. 4756–4759, Aug. 1980.

Kenneth C. Ehrlich et al., "Artificial Capillary Perfusion Cell Culture: Metabolic Studies", In Vitro, vol. 14, No. 5, 1978, pp. 443–450.

B. R. Jordan et al., "Transformation of Murine LMTK–Cells with Purified HLA Class I Genes", Immunogenetics , 18:165–171, 1983.

E. Morioka et al, "Purification of a granulocyte colony–stimulating factor from the conditioned medium of a subclone of human bladder carcinoma cell line 5637, HTB9", Res. Exp. Med. (1990), 190;229–238.

Steven A. Rosenberg et al., "In Vitro Growth of Murine T Cells II: Growth of a In Vitro Sensitized Cells Cytotoxic for Alloantigens", The Journal of Immunology, vol. 121, No. 5 Nov. 1978, pp. 1951–1955.

James Frank Parsons et al., "In Vitro Cell Perfusion. 1. System for Continuous Observation of Cells and Analysis of Perfusion Fluid Suitable for Isolated Mast Cell and Macrophage Studies", Journal of Pharmacological Methods vol. 8 pp. 073–089 (1982).

S. R. Adamson et al., "Industrial Mammalian Cell Culture", The Canadian Journal of Chemical Engineering, vol. 64, Aug. 1986, pp. 531–539.

Avshalom Mizrahi, "Production of Biologicals from Animal Cells an Overview", Process Biochemistry, (Aug. 1986), pp. 108–112.

Eastment and Rusceth, "Evaluation of Hematopoietic in Long–Term Bone Marrow Culture: Comparison of Species Differences" In Long–Term Bone Marrow Culture, Kroc oundation Series vol. 18, Proceeding of a Symposium Held at the Kroc Foundation Santa Ynex Valley, California, Sep. 12–16, 1983.

Connie J. Eaves et al., "Methodology of Long–Term Culture of Human Hemopoietic Cells", J. Tiss. Cull. Meth 13:55–62, 1991.

R. Ian Freshney, "Culture of Animal Cells A Manual of Basic Technique", (1987) Department of Medical Oncology Cancer Research Campaign Laboratories University of Glasgow, Second Addition, pp. 305–307, Alan R. Liss, Inc. (New York).

Yu–Chung Yang et al., "Human IL–3 (Multi–CSF): Identification by Expression Cloning of a Novel Hematopoietic Growth Factor Related to Murine IL–3", Cell, vol. 47, pp. 3–10, Oct. 10, 1986.

* cited by examiner

HUMAN LINEAGE COMMITTED CELL COMPOSITION WITH ENHANCED PROLIFERATIVE POTENTIAL, BIOLOGICAL EFFECTOR FUNCTION, OR BOTH; METHODS FOR OBTAINING SAME; AND THEIR USES

The present application is a Continuation Application of U.S. Ser. No. 09/027,671 filed Feb. 23, 1998.

BACKGROUND OF THE INVENTION

1. Field of the Invention

The present invention relates to methods for culturing lineage committed human cells, the cells thus obtained, and their uses.

2. Description of the Background

There is significant interest using both early and lineage committed cells for a variety of therapeutic purposes.

In tissue engineering, the goal is to reconstitute fully or partially functioning human tissue in vitro to enable a variety of clerical and other applications. Several studies have been carried out that are aimed at reconstituting functioning human tissues in vitro. Illustratively, the cultivation of human skin has been successful.

The hematopoietic system exemplifies the broad range of cells involved in protection of mammalian hosts against pathogens, toxins, neoplastic cells, and other diseases. The hematopoietic system is believed to evolve from a single stem cell, from which all the lineages of the hematopoietic system derive. Hematopoietic cells have been used in human therapy. Methods and apperati for culturing precursor hematopoietic cells to obtain desired mature hematopoietic cells have been described. See, U.S. Pat. Nos. 5,605,822, 5,399,493; 5,437,994; 5,459,069; 5,635,386, 5,670,147 and 5,670,351.

Adoptive cell therapy is the ex vivo expansion and re-infusion of immune effector cells into human recipients for the treatment or prevention of disease (Rosenberg et al., Science 233, 1318 (1986)). Developments in T-lymphocyte-based adoptive immunotherapy have lead to significant advances in the treatment of metastatic cancer (Rosenberg et al., Science 233, 1318 (1986); Rosenberg et al., N. Eng. J. Med. 319, 1676 (1988); Rosenberg et al., N. Eng. J. Med. 323, (1990)) and viral diseases including Epstein-Barr Virus (EBV) (Heslop et al. 1996), cytomegalovirus (CMV) (Riddell et al., Science 257, 238 (1992)) and human imunodeficiency virus (HIV) (Whiteside et al., Blood 81, 2085 (1993); Ridell et al., Hum. Gen. Ther. 3, 319 (1992)) in humans. Multiple patient populations have been identified in which T-cell therapy has achieved a response rate of approximately 34% after administration of tumor infiltrating lymphocytes (TILs) to metastatic melanoma patients (Rosenberg et al., J. Natl. Cancer Inst. 86, 1159 (1994)). A target human therapeutic dose of $10^{10}$–$10^{11}$ TLs is suggested based on extrapolation from studies in mouse tumor models and clinical experience (Topalian et al., J. Immunol. Meth. 102, 107 (1987)). Clinical responses to melanoma tumors have been obtained after expansion ex vivo of TILs in medium containing interleukin-2 (IL-2) and re-infusion of greater than $10^{11}$ T-cells per treatment cycle together with high doses of exogenous IL-2 (Rosenberg et al., N. Eng. J. Med. 319, 1676 (1988); Rosenberg et al. 1994). The enhanced anti-tumor activity of TILs in vivo compared to lymphokine activated killer (LAK) cells or NK cells may be a function of several complex processes including the ability of these T-cells to proliferate and release an array of lymphokines, to recirculate and accumulate at sites of tumor growth, and to specifically recognize and lyse autologous tumor cells (Pockaj et al. 1994; Rosenberg et al. 1994).

Dendritic cells (DCs) are highly specialized bone-marrow derived antigen presenting cells (APCs) which function as potent stimulating cells for primary T-lymphocyte-mediated immune response. Dendritic cell based immunotherapy is an emerging treatment strategy involving ex vivo expansion and reinfusion of antigen-pulsed or genetically modified DCs into human patients to vaccinate against cancer or infectious diseases. Clinical implementation of these therapies requires the capability of product sufficient quantities of functional DCs for effective patient treatment.

The use of cultured human cells in human therapy has required that a quantity of active cells sufficient to provide a therapeutic effect upon infusion into the patient be used. This has required using culture systems providing large numbers of cells. There is therefore a need for methods for obtaining lineage committed cells with augmented proliferative potential, biological function, or both since such methods would provide more potent cell compositions, capable of being used in smaller amounts in therapy.

SUMMARY OF THE INVENTION

Accordingly, it is an object of this invention to provide novel methods, including culture media conditions, for obtaining human lineage committed cells with enhanced proliferative potential, biological function, or both.

It is another object of this invention to provide cultured human lineage committed cells having enhanced proliferative potential, biological function, or both.

These objects and others may be accomplished by a method for obtaining lineage committed human cells having enhanced proliferative potential, biological function, or both. In this method, lineage committed human cells are cultured in any physiologically acceptable liquid culture medium conditions with the liquid culture medium being replaced.

DESCRIPTION OF THE PREFERRED EMBODIMENTS

Figure 1A:
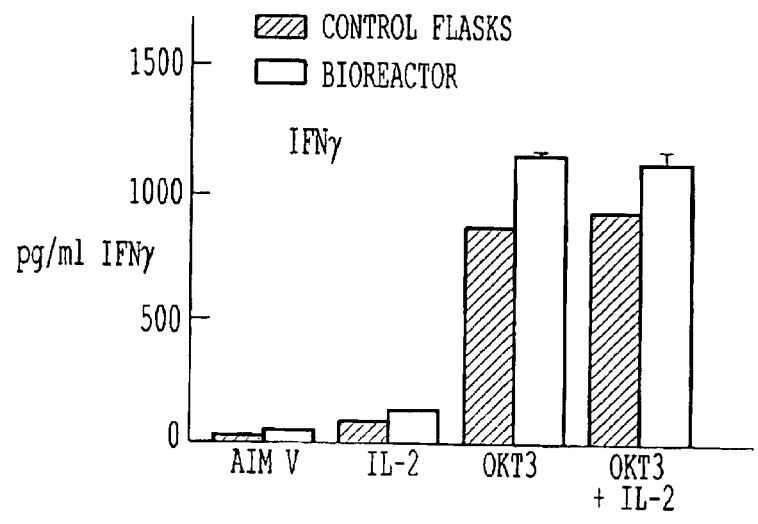
FIG. 1 shows the amount of cytokine produced after stimulation of T-cells cultured using continuous medium exchange conditions according to the present invention and cells cultured under standard static low density medium conditions. AIM V represents a control with in no added stimulus, all experiments were cultured with AIM V culture medium. OKT3 represents anti-CD3 mAb. (A) IFN-γ production; (B) TNF-α production; (C) GM-CSF production; (D) IL-10 production.
Figure 1B:
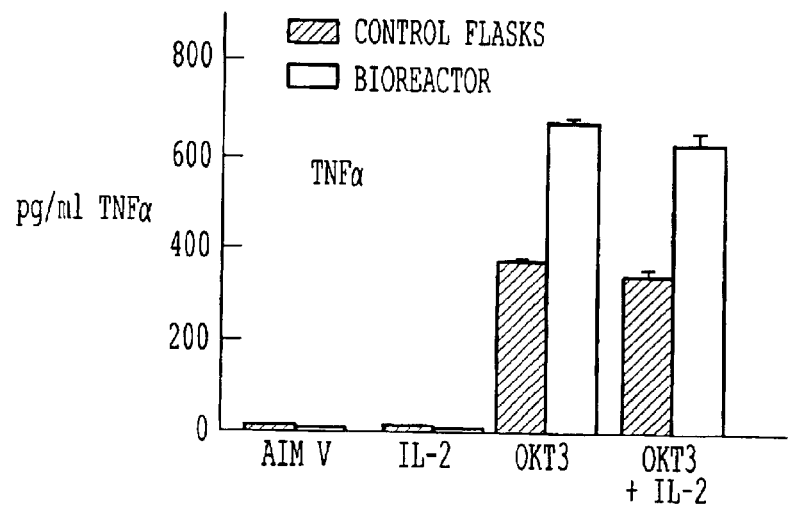
Figure 1C:
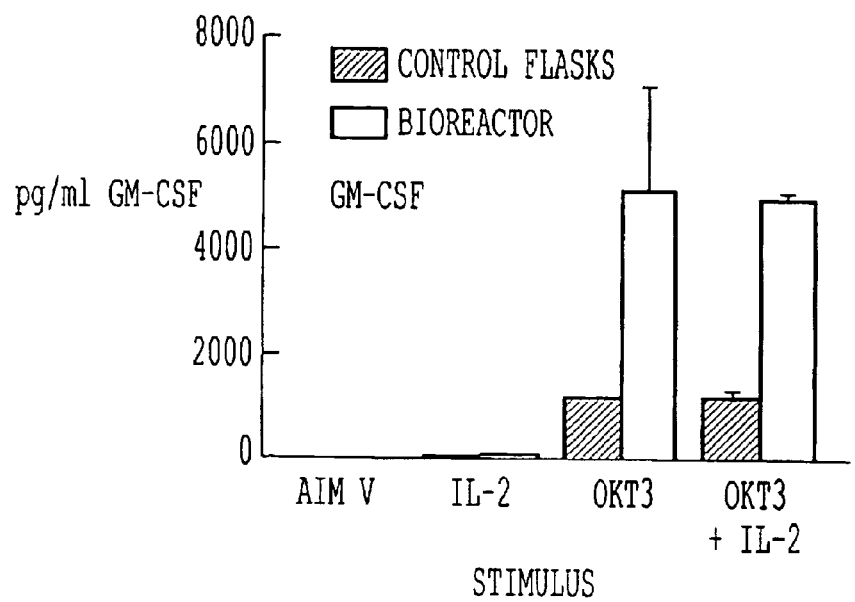
Figure 1D:
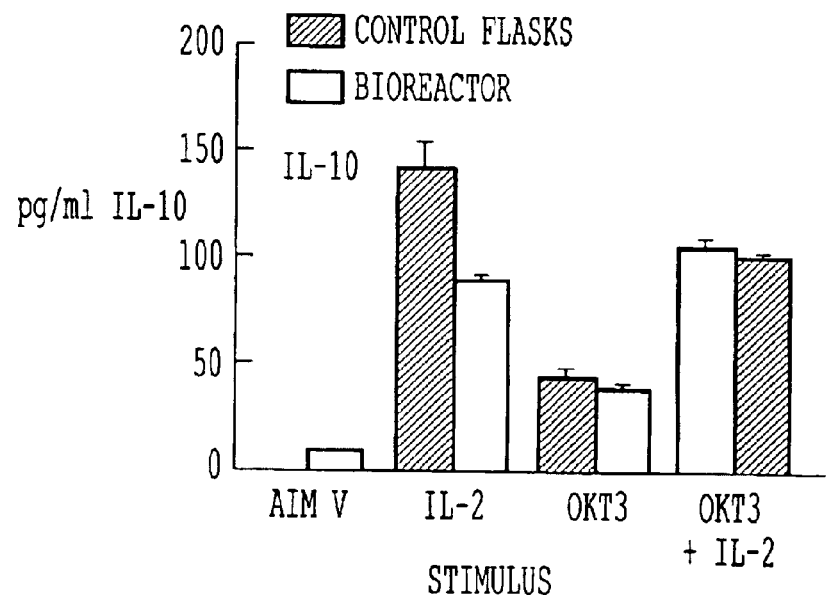

The present invention applies to the culture of lineage committed human cells using any known culture techniques. The invention is based on the discovery that by replacing the liquid culture media in any lineage committed human cell culture without substantially changing the cell density, it is possible to obtain cells having an enhanced proliferative potential, an enhanced biological function, or both. The cell Is obtained in accordance with the invention have enhanced proliferative potential as compared to the cells prior to culture and/or as compared to cells one obtains using otherwise identical culture conditions except that the liquid culture media is replaced by diluting the culture to achieve a lower cell density. Similarly, the biological function of the cells obtained in accordance with the invention is enhanced as compared with the biological function of these same cells prior to culture and/or as compared to the biological function of the same type of cells cultured under otherwise identical culture conditions except that the liquid medium is not replaced.

The cells one obtains in accordance with the invention are, by virtue of their enhanced proliferative potential and/or biological effector function, more potent. The present invention permits using a smaller number of lineage committed human cells to obtain similar or better results than one obtains using lineage committed human cells cultured in accordance with techniques existing prior to the present invention. The lineage committed human cells one obtains in accordance with the invention can be used in any application in which lineage committed human cells are used, including, but not limited to, therapy treatments including adoptive immunotherapy with effector cells, tumor specific cytotoxic T-cells, infectious disease specific cytotoxic T lymphocytes, cytokine induced killer cell therapy, antigen presenting cells to either tumor or infectious diseases, dendritic cells, antigen primed dendritic cells, tumor vaccines, genetically modified attenuated tumor cells, genetically modified antigen presenting cells, structural repair procedures such as cartilage defect repair, bone defect repair, tissue repair, would healing, burn care, solid organ repair, neurological defect repair, etc. Derivation and expansion of antigen specific T-cell populations including, but not limited to, viral (e.g. EBV, HPV, CMV, HIV, influenza) and tumor reactive T-cells, ex vivo expansion of human tumor infiltrating lymphocytes (TILs) for adoptice cancer immunotherapy, derivation and ex vivo expansion of cytokine induced killer (CIK) cells for rejection of human tumors including leukemia, lymphoma, breast and other cancers. Also, immunotherapy after autologous or allogeneic bone marrow transplantation. With dendritic cells: antigen presenting cell (APC)-based vaccines to stimulate T-cell responses in vitro or in vivo against simple or complex antigens including, but not limited to, tumor, viral, fungal and bacterial antigens. Therapy may include treatment or prevention of disease in normal individuals or human cancer patients.

Lineage Committed Cells

The lineage committed human cell used in accordance with the present invention are cells which are differentiated to at least a point where they are programmed to develop into a specific type of cell. These cells are not necessarily terminally differentiated. For example, CFU-GEMM cells are committed to develop, ultimately, into mature myeloid cells. Similarly, CFU-L cells are committed to develop into lymphoid cells. Accordingly, the lineage committed cells may be multipotential stem cells or committed progenitor cells. Of course, the lineage committed cells may be mature cells derived from these precursors. As used herein, the term "mature cells" refers to cells which are terminally differentiated. In one embodiment, the lineage committed cells are more differentiated than human stem cells. In another embodiment, the lineage committed cells are more differentiated than progenitor cells. In yet another embodiment, the lineage committed cells are mature cells. A discussion of cell development for blood cells and lymphocytes is provided by S. McKenzie, *Hematology*, Second Edition, William and Wilkins, 1996, pp. 9–30 and 55–89.

The types of lineage committed cells used in the present method may vary widely. Any type of lineage committed cell which may benefit from medium replacement may be used in the present invention. Preferred cells which can be used include human hematopoietic cells, mesenchymal cells, dendritic cells, fibroblasts, hepatocytes, neural cells, epithelial cells, lymphocytes, keratinocytes, osteoblasts or osteoclasts. Specific examples of suitable human hematopoietic cells include megakaryocytes, monocytes, neutrophils, basophils, eosinophils, tumor specific cytotoxic T lymphocytes, cytokine induced killer cells, antigen presenting cells to either tumor or infectious diseases, dendritic cells, antigen primed dendritic cells, leukocyte precursor, and neutrophils. Suitable examples of mesenchymal cells include, chondrocytes, osteoblasts, myeoblasts, fibroblasts, tenoblasts, stromal cells (e.g., from bone marrow), tenocytes, adipocytes, osteocytes and myocytes. Suitable examples of lymphocytes include T-cells and B-cells. Pre-T and pre-B cells are also suitable. The T-cells ($CD3^+$) may be $CD8^+$ or $CD4^+$ cells, or cells derived from said populations.

In one embodiment of the present invention, the lineage committed cells may be stem cells (e.g., hematopoietic or stromal stem cells), progenitor cells (e.g., hematopoietic progenitors), mature myeloid cells, or stromal cells (e.g., from bone marrow). In another embodiment, the cells may be dendritic cells (e.g., myeloid- or lymphoid-derived) or non-myeloid mature cells which are other than stromal cells (e.g., the mature cells described above, especially T-cells or chondrocytes).

The cells used in the present method may be obtained from a variety of sources using well-known techniques, see Heslop HE, Ng Cyc, Li C, Smith CA, Loftin SK, Krance Ra, Brenner MK, Rooney CM: Long-term restoration of immunity against Epstein-Barr virus infection by adoptive transfer of gene-modified virus-specific T lymphocytes. Nature Med 2:551, 1996; Lu P,Negrin RS: A novel population of expanded human CD3+CD56+cells derived from T-cells with potent in vivo antitumor activity in mice with severe combined immunodeficiency. J immunol 153:1687, 1994; Romani N, Gruner S, Brang D, Kampgen E, Lenz A, Trockenbacher B, Konwalinka G, Fritsch PO, Steinman RM, Schuler G: Proliferating dendritic cell progenitors in human blood. J. Exp Med 180:83, 1994; Rosenberg SA, Spiess P, Lafreniere R: A new approach to the adoptive immunotherapy of cancer with tumor-infiltrating lymphocytes. Science 233:1318, 1986.

When culturing T-cells, for example, a human hematopoietic cell composition enriched in T-cells may be used. Such a composition may be enriched in T-cell content by any desired amount, such as by up to $10^3$ fold or more. Different, known methods may be used to achieve this enrichment, corresponding either to a negative selection method or a positive selection method. For example, in accordance with the negative selection method, mature cells are isolated using immunological techniques, e.g., labeling non-progenitor, non-stem cells with a panel of mouse anti-human monoclonal antibodies, then removing the mouse antibody-coated cells by adherence to rabbit-anti-mouse Ig-coated plastic dishes. See, for example, Emerson et al, J. Clin. Invest. (1985) 76:1286–1290.

In one embodiment of the present invention, the lineage committed cells used in the present invention may be substantially free of stem and progenitor cells. As discussed above, the lineage committed cells are other than human bone marrow stromal cells. In another embodiment, the lineage committed cells may be other than mesenchymal cells.

Enhanced Proliferative and Biological Function

As used herein, the term "proliferative potential" refers to the ability of a cell population to divide and thereby produce more cells of the same or more differentiated type. Accordingly, the proliferative potential of a cell population may be determined by culturing the cells and then determining the degree of expansion of the original cell population. By culturing the lineage committed cells in a medium that is replaced product cells are obtained which have enhanced proliferative potential. This means that the product cells have a greater ability to produce more cells as compared to the cells that were used at the beginning of the culturing. In a particularly preferred embodiment, the product cells of the present invention have a greater ability to replicate or further differentiate to the desired cell type as compared to the same cells which have been cultured at low densities in a static culture.

Static culture conditions for the comparative purposes are conditions employing the same medium, same starting cell inoculum source except grown without frequent medium exchange.

For example, the T-cell concentration in a conventional low density culture is allowed to reach a maximum of $2-4 \times 10^6$ cells/ml during cell growth with time. After growth to this maximum density, the cell concentration is reduced to $5 \times 10^5$ cells/nil and the cells are allowed to grow again to $2-4 \times 10^6$ cells/ml. This cycle of growth to maximum cell density followed by a reduction of $5 \times 10^5$ cells/ml is repeated throughout the entire culture period.

In contrast, in the method of the present invention for culturing T-cells, the cell density is not substantially reduced or adjusted at any time during the culture period. Thus, T-cells grow to maximum cell densities of $2-4 \times 10^6$ cells/ml under conditions of culture medium replacement.

For the cultured cells of the present invention (e.g., T-cells) the cells having enhanced proliferative potential expand at least 5-fold expansion when cultured in a static culture using a T-flask (see Example 2 below). More preferably, the T-cells of the present invention expand at least 10-fold, even more preferably at least 25-fold. Using the method of the present invention T-cells which expand at least 40, 75, 100, and 150-fold in the secondary static culture may be obtained. Even higher proliferative potentials, e.g., at least 200, 500, 1000 or 2000-fold expansion in the secondary culture may be observed using the method of the present invention.

The term "biological function" refers to the ability of a cell population to carry out its biological mission, i.e., to perform its recognized biological purpose in vivo. As one skilled in the art will readily appreciate, the biological function of a cell population is determined by the nature of the lineage committed cells that are being cultured. Therefore, the biological function of one cell population may be quite different from another.

Examples of biological function include secretion of substances (such as cytokines, hormones, antibodies, etc.), cell-cell communication, receptor expression on the cell surface, cytolysis, antigen presentation, antigen processing, ability to home in vivo to sites for function, ability to proliferate leading to development/regeneration of tissue similar to naturally occurring structure/function.

For example, the biological function of T-cells are cytolysis and secretion of cytokines such as IFN-$\gamma$, IL-10, TNF-$\alpha$ and GM-CSF. By replacing the medium during culturing, cells having enhanced biological function may be obtained. Thus, the cell products of the present invention have a greater biological function as compared to the cells used at the beginning of the culture. In a particularly preferred embodiment, the product cells have a greater biological function as compared to the same cells cultured under static medium culture conditions. The biological function of a cell population may be determined by measuring the amount of a particular response, e.g., cytokine secretion, and quantifying the amount of response on a per cell basis. The cells cultured according to the present invention may have a biological function which is enhanced at least 1.2-, 1.5-, 2-, 3-, 4-, 5-, 10-, 20-, 50-, 75-, 300-, 350-, 400-, 450- or 500-fold, as compared to cells cultured without medium replacement (i.e., cells cultured under static medium culture conditions).

It is important to note that the replicative potential or biological function of a cell population is a property of the population considered as a whole. For example, even in the cells produced by the present invention it is possible that some of the cells in the population may not divide or effect a biological function. However, on average, the cells produced according to the present invention have greater replicative potential, biological function, or both, as compared to cells produced according to low density static culture procedures. In addition, cells may have a variety of biological functions. For example, a cell may secrete multiple cytokines. In the present invention, the cells may have one enhanced biological function, e.g., the secretion of one cytokine is enhanced. Alternatively, multiple biological functions may be enhanced.

In one embodiment, the cells produced according to the present invention have enhanced replicative potential. In another embodiment, the cells have enhanced biological function. In still another, and preferred embodiment, the cells obtained by the present method have both enhanced replicative potential and enhanced biological function. As compared to cells cultured in a static medium, the cells produced according to the present invention preferably have at least a two-fold greater replicative potential and/or biological function. More preferably at least five-fold, and, most preferably at least ten-fold greater replicative potential and/or biological function as compared to cells cultured in static culture. This enhanced replicative potential and/or biological function may be determined after the cells are isolated. The inventors have discovered that after isolating the cells produced under conditions of medium replacement the cells can be recultured (i.e., a secondary culture) in, for example, a static medium and the enhanced replicative potential and/or biological function may be observed. Accordingly, the cells produced according to the present method are expected to demonstrate enhanced replicative potential and/or biological function after infusion into a patient.

Culture Medium and Environment

The lineage committed cells may be cultured in any known physiologically acceptable liquid culture medium, i.e., a medium which supports the cell viability and proliferation, using any conditions as long as media replacement conditions are used. Of course, the composition of the media may vary with the cell type being cultured. Media suitable for culturing specific cells are well-known, for example, see Schmidt-Wolf IGH, Negrin RS, Kiem H, Blume KG, Weissman IL: Use of a SCID mouse/human lymphoma model to evaluate cytokine-induced killer cells with potent antitumor cell activity. J. Exp Med 174:139, 1991; Morse MA, Zhou LJ, Tedder TF, Lyerly HK, Smith C: Generation of dendritic cells in vitro form peripheral blood mononuclear cells with granulocyte-macrophage-colony-stimulating factor, interleukin-4, and tumor necrosis factor-alpha for use in cancer immunotherapy. Ann Surg. Jul 1; 226:16, 1997; Romani N, Grunner S, Brang D, Kampgen E, Lenz A. Trockenbacher B, Konwalinka G, Fritsch PO, Steinman RM, Schuler G: Proliferating dendritic cell progenitors in human blood. J. Exp Med 180:83, 1994.

The culture medium contains organic and inorganic components required for cell proliferation and may contain standard known medium components such as, for example, AIM V, IMDM, MEM, DMEM, RPMI 1640, Alpha Medium or McCoy's Medium, which can use combinations of serum albumin, cholesterol and/or lecithin selenium and inorganic salts. As known, these cultures may be supplemented with corticosteroids, such as hydrocortisone at a concentration of $10^{-4}$ to $10^{-7}$ M, or other corticosteroids at equal potent dose, such as cortisone, dexamethasome or solumedrol. The cultures are typically carried out at a pH which is roughly physiologic, i.e., 6.9 to 7.4. The medium is typically exposed to an oxygen-containing atmosphere which contains from 4 to 20 vol. percent oxygen, preferably 6 to 8 vol. percent oxygen.

Illustratively, the medium used in accordance with the invention may comprise one or more basic components. The first component is a media component comprised of AIM V, IMDM, MEM, DMEM, RPMI 1640, Alpha Medium or McCoy's Medium, or an equivalent known culture medium component. The second is a serum component which comprises at least horse serum or human serum and may optionally further comprise fetal calf serum, newborn calf serun, and/or calf serum. The third component is a corticosteroid, such as hydrocortisone, cortisone, dexamethasome, solumedrol, or a combination of these, preferably hydrocortisone.

The compositional make up of various media which can be used in the present invention are well-known, see U.S. Pat. No. 5,635,386, columns 11–30; Lewko WM, Good RW, Bowman D, Smith TL, Oldham RK: Growth of tumor derived activated T-cells for the treatment of cancer. Cancer Biotherapy, vol 9, No. 3, pp 221, 1994; Freedman RS, Tomasovic B, Templin S, Atkinson EN, Kudelka A, Edwards CL, Platsoucas CD: Large-scale expansion in interleukin-2 of tumor-n infiltrating lymphocytes from patients with ovarian carcinoma for adoptive immunotherapy: J. Immunol Methods 167:145–160, 1994.

The serum component may be present in the culture in an amount of at least 1% (v/v) to 50% (v/v). The serum concentration may be preferably in the neighborhood of 15 to 30% (v/v). For higher serum concentrations, the exchange rate is increased proportionately. The third component may be present in an amount of from $10^{-7}$ M to $10^{-4}$ M, and is preferably present in an amount of from $5\times10^{-6}$ to $5\times10^{-5}$ M. The media component represents the balance such that all three components add up to 100%. Alternatively the serum component can be replaced by any of several standard serum replacement mixtures which typically include insulin, albumin, and lecithin or cholesterol. See, Migliaccio, et al, Exp. Hematol. (1990) 18:1049–1055, Iscove et al, Exp. Cell Res. (1980) 126:121–126, and Dainiak et al, J. Clin. Invest. (1985) 76:1237–1242.

Cell Density

The cell density in the present method may vary widely. Preferably, the cell density is $10^4$ to $10^8$ cells per ml of culture. More preferably, the cell density is T-cells inoculum: $5\times10^4$/ml to $2\times10^6$/ml; T-cells final density: $5\times10^6$ to $5\times10^7$/ml; dendritic cells: $1\times10^6$ cells/cm$^2$ ($3.33\times10$–$3.33\times10^7$ cells/ml) (inoculum density); T-cells inoculum: starting population of 40–80 million cells (0.16 –0.32 –$10^6$ cells/ml; harvest: 12–32 –$10^6$ cells/ml, $10^8$ cells/ml; CIK: inoculum density=$1\times10^6$ cells/ml; density at harvest: 12 –$42\times10^6$ cells/ml. The CD34+selected inoculum density for derivation of dendritic cells is 3.33–33.3 cells/cm$^2$ or $10^4$–$10^5$ cells/ml.

Growth Factors

Another, optional but important, embodiment of the present invention, resides in the addition of growth factors (e.g., hematopoietic growth factors), including synthetic hematopoietic growth factors, to the medium-exchanged cultures. Of course, the growth factors are selected according to the nature of the lineage committed cells being cultured. The particular growth factors which stimulate a given cell type in cell culture are well-known, see for example, Romani N, Gruner S, Brang D, Kaampgen E, Lenz A, Trockenbacher B, Konwalinka G, Fritsch PO, Steinman RM, Schuler G: Proliferating dendritic cell progenitors in human blood. J. Exp Med 180:83, 1994; Maraskovsky E, Brasel K. Teepe M, Roux ER, Lyman SD, Shortman K, McKenna HJ: Dramatic increase in the number of functionally mature dendritic cells in Flt3 ligand-treated mice: multiple dendritic cell subpopulations identified. J. Exp Med 184:1953, 1996; Sallusto F, Lanzavecchia A: Efficient presentation of soluble antigen by cultured human dendritic cells is maintained by granulocyte/macrophage colony-stimulating factor plus interleukin 4 and downregulated by tumor necrosis factor alpha. J. Exp Med 179:1109, 1994; Santiago-Schwartz F, Divaris N, Kay C, Carsons SE: Mechanisms of tumor necrosis factor-granulocyte-macrophage colony-stimulating factor-induced dendritic cell development Blood 82:3019, 1993; Siena S, Di Nicola M, Bregni M. Mortarini R, Anichini A, Lombardi L, Ravagnani F, Parmiani G, Gianni Am: Massive ex vivo generation of functional dendritic cells from mobilized CD34+ blood progenitors for anticancer therapy. Exp Hematol 23:1463, 1995; Rosenberg SA, Spiess P, Lafreniere R: A new approach to the adoptive immunotherapy of cancer with tumor-infiltrating lymphocytes. Science 233:1318, 1986; Rosenberg SA, Packard BS, Aebersold PM, Solomon D, Topalian SL, Toy ST, Simon P, Lotze MT, Yang JC, Seipp CA, Simpson C, Carter C, Bock S, Schwartzentruber D, Wei JP, White DE: Use of tumor-infiltrating lymphocytes and interleukin-2 in the immunotherapy of patients with metastatic melanoma. New Engl J. Med 319:1676, 1988; Schmidt-Wolf IGH, Negrin RS, Kiem H, Bluime KG, Weissman IL: Use of a SCID mouselhuman lymphoma model to evaluate cytokine-induced killer cells with potent antitumor cell activity. J. Exp Med 174:139, 1991.

It is widely known that IL-2 is preferably used in the culturing of T-cells. The amount of IL-2 in the culture medium may vary widely. Preferably, the IL-2 concentration is 25 to 1,000 IU/ml. GM-CSF, IL4, TNF-α, Flt3-L, or combinations thereof, are preferably added to the culturing medium when expanding dendritic cells. General copicentration ranges for cytokines in dendritic cell culture media are: GM-CSF: 50 ng/ml (1 to 500 ng/ml); IL4: 25 ng/ml (1 to 500 ng/ml); TNFα: 25 ng/ml (1 to 500 ng/ml); Flt3L: 25 ng/ml (1 to 500 ng/ml). These ranges include all specific values and subranges.

Other growth factors which may be added to the culture medium include the cytokines IL-3 and GM-CSF alone or together at a rate of from 0.1 to 100 ng/ml/day, preferably about 0.5 to 10 ng/ml/day, most preferably 1 to 2 ng/ml/day. Epo may be added to the nutrient medium in an amount of from 0.001 to 10 U/ml/day, preferably 0.05 to 0.15 U/ml/day. Mast cell growth factor (MCGF, c-kit ligand, Steel factor), may be added to the medium in an amount of from 1 to 100 ng/ml/day, preferably 10 to 50 ng/ml/day. IL-1 (α or β) may also be added in an amount of from 10 to 100 units/ml per 3 to 5 day period. Additionally, IL-6, G-CSF, basic fibroblast growth factor, IL-7, IL-8, IL-9, IL-10, IL-11, PDGF, or EGF to be added, at a rate of from 1 to 100 ng/ml/day.

Medium Replacement

The present invention relies on first culturing the lineage committed cells in a liquid culture medium which is replaced, preferably perfused, either continuously or periodically. The rate of medium replacement may be at least 25% daily replacement, preferably at least 50% daily replacement, and may be 25% to 100% daily replacement for a cell density of from $1 \times 10^4$ to $1 \times 10^7$ cells per ml of culture. For cell densities higher than $10^7$ cells per ml, the medium exchange rate may be increased proportionally to achieve a constant medium and serum flux per cell per unit time. For cell densities lower than $10^7$ cells per ml, the medium exchange rate may likewise be decreased proportionately. The medium replacement rate may vary during the culturing. In one embodiment, the replacement rate is relatively low at the beginning of the culturing and then increased as the cell density in the culture increases.

Replacement of the nutrient medium in accordance with the invention may be carried out in any manner which will achieve the result of replacing the medium, e.g., as described in U.S. Pat. No. 5,646,043. The flow of the aliquot being added may be by gravity, by pump, or by any other suitable means. The flow may be in any direction or multiplicity of directions, depending upon the configuration and packing of the culture. Preferably, the new medium is added to the culture in a manner such that it contacts the cell mass. Most preferably, it is added the culture in a manner mimicking in vivo perfusion, i.e., it is perfused through at least part of the a cell mass and up to the whole cell mass.

The metabolic product level in the medium is normally maintained within a particular range. Glucose concentration is usually maintained in the range of about 5 to 20 mM. Lactate concentration is usually maintained below 35 mM, preferably below 0.5 mg/ml. Glutamine concentration is generally maintained in the range of from about 1 to 3 mM. Ammonium concentration is usually maintained below about 2.4 mM. These concentrations may be monitored by either periodic or on-line continuous measurements using known methods. See e.g., Caldwell et al, J. Cell. Physiol. (1991) 147:344–353.

In a preferred embodiment of the invention, the culture medium is continuously perfused to provide fresh medium at a rate which is proportional to the lactate concentration and/or the cell density in the culture. Preferably, this medium replacement is accomplished without diluting the cell density of the culture.

Culture Times

The culture time may vary widely. The cells are preferably cultured for at least the minimum amount of time required to produce cells with enhanced replicative potential, biological function, or both. This time may vary with cell type, depending on the cell doubling time. In preferred embodiment, the cells are cultured according to the invention for at least 2 days, more preferably, at least 4 days. The maximum culture time is not particularly limited. For example, the cells may be cultured for up to 10 days, up to 25 days, up to 50 days, up to 75 days, up to 100 days, or longer, if desired (>100 days [e.g., T-cells, Rosenberg]).

Cell Culture Apparatus

An obstacle with ex vivo expansion has been the ability to reliably generate large quantities of ex vivo expanded lineage comunitted cells in a controlled process for effective therapy. The traditional cell expansion methods in bags, flasks or roller bottles involves multi-step manual cell culture processes. Due to the lack of continuous medium perfusion features, the cell concentrations are maintained at a low level ($\sim 1 \times 10^6$ cells/ml) by the addition of fresh medium to the culture-container or by transferring part of the culture to additional culture containers. Such procedures require numerous aseptic transfers resulting in less reproducible and reliable performance and increased risk of contamination or critical operator error.

In a preferred embodiment, an automated clinical-scale cell production system (CPS), which has been developed to process and expand cells in a closed and sterile environment and which is described in allowed U.S. application serial no. 081478,622 incorporated herein by reference, is used. This is capable of exchanging medium at a continuous rate without removal of cells. The use of the CPS requires a single aseptic transfer and is microprocessor controlled, resulting in significant savings in labor and space.

The CPS has been automated by incorporating microprocessor controlled hardware and the development of software to run the processes. The CPS embodies a modular, closed-system process comprised of a pre-sterilized, single-use disposable cell cassette operated by automated instruments. The instrumentation components of the system include an incubator unit and processor unit, along with a computer based system manager.

The cell cassette provides a closed, sterile environment in which cell production can occur. The single-use cartridge is provided fully assembled in a sterile package, opened just prior to use. The sterile pathway contained in the cell cassette includes: cell growth chamber, medium supply container, a pump for delivery of components, and sterile barrier elements throughout.

A dedicated, small incubator controls the biological and physical environment and operations of each cell cassette necessary to support the cell growth process. The incubator receives and self-engages the disposable cell cassette, much like a VCR and videocassette. The incubator controls: the flow of medium to the growth chamber, the temperature (4° C.) of the growth medium supply compartment, the temperature (37° C.) of the growth chamber compartment, and the concentration and flow rate of gases delivered to the gas compartment of the culture chamber. The incubator also monitors various safety-alarm parameters to assure that the cell production process is proceeding as expected. In the unlikely event of failure of an incubator, the cell cassette, is readily transferred to another incubator with minimal interruption of the culture process.

The processor performs the initial priming of the cell cassette with growth medium and, through instructions to the operator, the controlled inoculation of cells. The same unit also performs the removal (harvest) of the cells from the growth chamber at the completion of the cell production process, sterilely transferring the cells to a pre-attached harvest container (analogous to a blood transfusion bag).

The system manager employs a user-friendly graphical interface. The system manager provides a convenient central user interface and provides for redundant monitoring of each incubator in the network. The system manager can perform procedure scheduling (up to 50 incubators) tasks for the operators and provide a daily or weekly printed record of alarm events for quality control and record keeping purposes.

The ID key contains a semiconductor memory device and clock and is affixed to each cell cassette at the beginning of a cell production procedure. The ID key provides reliable identification of the cell product, instructs the instruments for the cell production process, prevents mix-ups and operator error, and stores the primary data for complete process history record (effectively a "manufacturing batch record" for the cell product).

Therapeutic Applications

After culturing according to the invention, the lineage committed human cells have enhanced replicative and/or biological function. The cultured cells may be isolated by harvesting them from the culture apparatus. The cells may be harvested by, for example, withdrawing the cells by syringe, or by continuously allowing the cells to flow out of the culture reactor, by the pressure produced by replacing the culture medium, through an exit tube. After harvesting, the cells may be infused in a patient to obtain the therapeutic benefits of the cultured cells.

The inventors have discovered that lineage committed cells cultured under conditions of medium exchange according to the present invention have an enhanced ability to replicatate and/or have enhanced biological function after the cells are isolated. Since the cells of the present invention have replicative and/or biological function, fewer cells may be required to achieve a given level of effectiveness as compared to cells that were cultured under static conditions.

The procedures for infusing the cells of the present invention for human therapy are well-known, see:
Anti-EBV Specific CTLs:
Heslop et al. New England Journal of Medicine 331:679–680 (1994),
Heslop et al. Nature Medicine 2:551–555 (1996), and
Heslop et al. Immunology Reviews 157:217–222 (1997);
*Adoptive Immunotherapy in Viral Diseases*
Riddell et al. Annual Reviews in Immunology 13:545–3159 (1991),
Anti-CMVCTLs, and
Walter et al. New England Journal of Medicine 333:1038–1044 (1995);
Anti-HIV CTLs
Levine et al. Science 272:1939–1943 (1996);
*Anti-Tumor CTLs*

Anichini et al. Journal of Immunology 156:206–217 (1996), Cardoso et al. Blood 90:549–561 (1997), and
Schultze et al. Blood 89:3806–3816 (1997); and
Dendritic Cells
Choudhury A, Gajewski, JL, Liang, IC, Popat, U, Claxton, DF, Kliche KO, Andreef M,
Champlin, RE, Blood 89:1133 (1997),
Girolomoni G, Ricciardi-Castagnoli, P: Immunol. Today 18, 102 (1997),
Hsu, FJ, Benike, C, Fagnoni F, Liles TM, Czerwinski D, Taidi B, Engleman, EG, Levy R,
Nature Med. 2: 52 (1996), and
Mayordomo 31, Zorina T, Storkus WJ, Zitvogcl, L, Garcia-Prats MD, DeLeo AB, Lotze MT:
Stem Cells 15: 94 (1997).

Having generally described this invention, a further understanding can be obtained by reference to certain specific examples which are provided herein for purposes of illustration only and are not intended to be limiting unless otherwise specified.

EXAMPLES

Example 1

Large Scale Ex Vivo Expansion of Human T-Lymphocytes

The growth of human T-lymphocytes in a CPS was demonstrated using a model system in which peripheral blood CD8$^+$ T-cells from normal donors were activated using PHA. CD8+ cells were inoculated into the CPS at a density of 20–80 million cells (0.08–10$^6$–0.32 ×10$^6$ cells/ml) in AIM-V medium containing 600 IU/ml of rIL-2. A yield of 3–8 billion cells (12×10$^6$ –32×10$^6$ cells/ml) (>90% viability) was obtained at harvest on day 10 (n=12). Continuous one pass perfusion of flesh medium enabled the CPS to maintain high cell densities and low lactate concentrations (<0.5 mg/ml). Under these conditions the total medium exchanged was 46 liters. Polyclonal T-cell expansion in CPS was demonstrated by flow cytometric analysis using a panel of 10 different T-cell receptor (TCR) Vα and Vβ-subfamily-specific mAbs. Each TCR family was represented at similar levels in the CPS cultures compared to conventional control T-flask cultures. Furthermore, harvested T-lymphocytes secreted IFN-γ (490–2300 pg/ml), TNF-α(190–880 pg/ml), GM-CSF (1900–5100 pg/ml) and IL-10 (5–35 pg/ml) in response to anti-CD3 mAb. These findings indicate that human T-cells expanded in the CPS are fully responsive to stimulation through the TCR. In conclusion, these studies demonstrate the potential of the CPS for large scale expansion of functional effector T-cells for use in human T-cell therapies.

Example 2

Enhancing the Proliferative Potential and Biological Effector Function of Human T-Lymphocytes The growth of PHA-activated human CD8$^+$T-cells was used as a model system for evaluating the effects of continuous perfusion on T-cell expansion. Human CD8$^+$T-cells were expanded using continuous one-pass perfusion with medium containing IL-2 in the CPS for ten days. The perfusion rates were increased with the increase in cell number such that lactate concentration in the spent medium was maintained at 0.5 mg/ml. The continuous perfusion of medium resulted in high density cultures of concentrations ranging from 12 to 32 million cells/ml starting from a population of 0.16–0.32 million cells/ml. Parallel T-flask cultures were set up at the same culture conditions (vis. inoculum density, culture depth, oxygenation, and medium composition). These cultures were semidepleted to $0.5 \times 10^9$ cells/ml when the cell densities reached $1.0 \times 10^9$ cells/ml by manual removal of spent medium and cells and replenishing with fresh medium. The ex vivo expanded T-cells harvested from the CPS and T-flasks on day 10 (also called primary cultures) were further expanded in presence of IL-2 for four days (secondary cultures) in a static culture medium. The results of the expansions from three experiments are shown in Table 1.

The expansion in the CPS during the ten days of primary culture was lower by 1.85–4.63 fold compared to T-flasks. However, subsequent evaluation (secondary culture) of the replicative potential of CPS and T-flask expanded cells revealed 12.7–42.2 fold higher expansion with the CPS derived cells in the secondary culture. In this secondary culture both the CPS-expanded and the T-flask-expanded cells were cultured under static medium conditions in a semidepleted T-flask. Thus, the overall expansion, i.e., after primary and secondary culturing, of CPS derived cells was 3.8–10.3 fold higher than in semidepleted T-flask cultures. These results demonstrate the benefit of continuous perfusion in enhancing the replicative potential of human $CD8^+$ cells.

The functionality of the T-cell harvested from the CPS or parallel T-flask cultures was assessed by analysis of cytokine release (see FIG. 1). T-cells harvested from the CPS or T-flasks produced similar concentrations of IFN-$\gamma$ in response to anti-CD3 mAb. In contrast, T-cells derived from the CPS produced higher concentrations of TNF-$\alpha$ and GM-CSF than T-cells derived from T-flasks. The data indicates that T-cells derived in the CPS are filly responsive to stimulation through the TCR-CD3 complex and may produce higher levels of particular cytokines on a per cell basis than T-cells produced in T-flasks.

Significance

The enhanced proliferative potential of T-cells derived in the CPS using continuous perfusion has important applications for the therapeutic efficacy of these T-cells after reinfusion. Effective adoptive immunotherapy for viral diseases and cancer requires the reliable generation of large quantities of functional cells capable of continued cell expansion in vivo together with recirculation and localization of effector T-cells at sites of various infection or tumor cell growth. Expansion of T-cells using continuous perfusion in the CPS results in large numbers of high quality effector T-cells with enhanced replication potential and effector function.

TABLE 1

Post-Expansion Replicative Potential

| Exp. | Device[1] | Primary Culture Fold Expansion (10 days) | Secondary Culture[2] Fold Expansion | Fold Expansion Overall[3] | Increased Relative Expansion in CPS |
|---|---|---|---|---|---|
| #1 | CPS | 65 | 40 | 2600 | 10.3 |
|  | T-flasks | 120 | 2.1 | 252 |  |
| #2 | CPS | 93 | 152 | 14136 | 9.1 |
|  | T-flasks | 431 | 3.6 | 1552 |  |
| #3 | CPS | 57 | 33 | 1881 | 3.8 |
|  | T-flasks | 190 | 2.6 | 494 |  |

[1]T-25 flasks; hemidepletion.
[2]Secondary culturing was conducted in T-25 flasks, hemidepletion, for both CPS- and T-flask expanded cells. The values indicate fold expansion after 4 days.
[3]Represents (fold expansion in primary culture) × (fold expansion in secondary culture)

Example 3

Clinical Scale Expansion of Human Dendritic Cells in a Continuously Perfused Bioreactor System The purpose of the present studies was to develop and implement a process for expansion of human dendritic cells (DCs) in a continuously perfused clinical scale bioreactor system. Experiments in small scale cultures were conducted to evaluate the effect of frequent medium exchange on dendritic cell expansion and function. Peripheral blood mononuclear cells (PB MNCs) from normal donors were inoculated at low ($1-10^6$ cells/cm$^2$) an high ($5 \times 10^6$ cells/cm$^2$) inoculum densities in T25 cm$^2$ flasks. Non-plastic adherent cells were gently removed after 2 hours at 37° C., and adherent cells comprising approximately 50% of the total inoculated cell population were cultured for 7 days. The cultures either were not fed, or received 50% fresh serum-free AIM V medium containing GM-CSF and IL-4 on days 2,4 and 6. TNF$\alpha$ was added on day 6 for the final 24 hours of culture. Cells from these cultures expressed the characteristic "veiled" morphology and surface phenotype of dendritic cells as determined by the cytometry.

Furthermore, DCs demonstrated at least 50-fold greater stimulating activity in the alloMLR compared to PB MNCs. Interestingly, frequent medium exchange, particularly at high inoculum density, significantly enhanced the stimulating activity of harvested DCs (>5-fold compared to static culture conditions. Total cell recovery correlated well with lactate produced per culture supporting the utility of lactate measurement as a non-invasive means to improve medium exchange protocols and monitor DC culture productivity. Initial experiments in a CPS at an inoculum density of $1.6-10^6$ cells/cm$^2$ produced $295.3-10^6$ dendritic cells at harvest on Day 7. Experiments are in progress to optimize the expansion and function of dendritic cells at high density in the CPS under condition of continuous medium perfusion. These studies demonstrate that continuous medium perfusion significantly improves the quantity and biological function of harvested DCs.

Figure 2A:
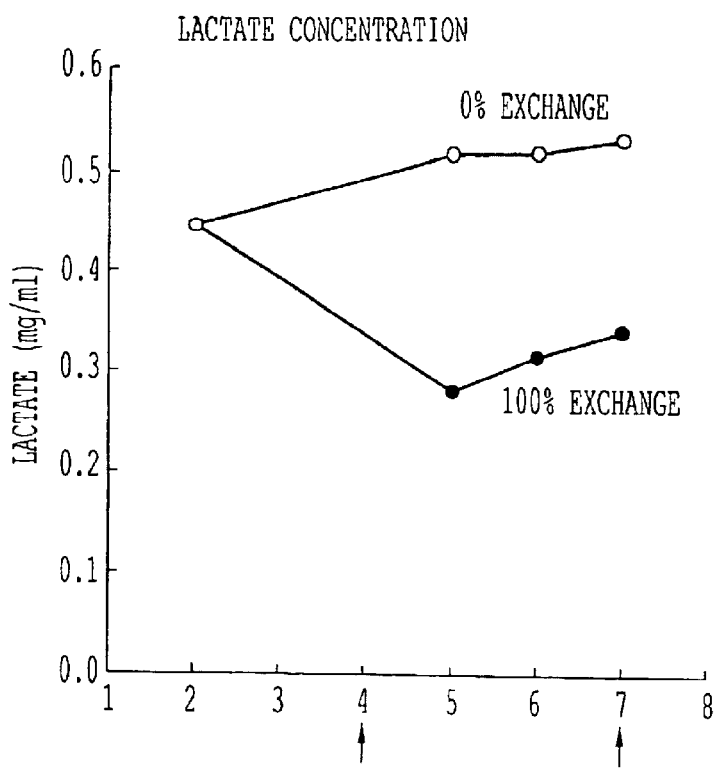
FIG. 2 shows (A) the lactate concentration during a dendritic cell culture according to the present invention (100% exchange) and in a static culture (0% medium exchange) at low inoculum density, and (B) the mixed leucocyte response (MLR) of the isolated dendritic cells.
Figure 2B:
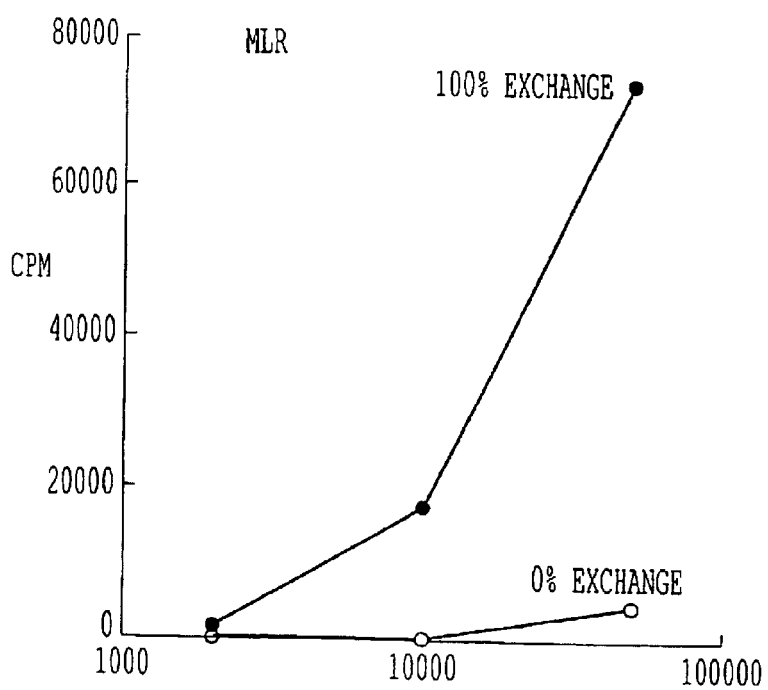
Figure 3A:
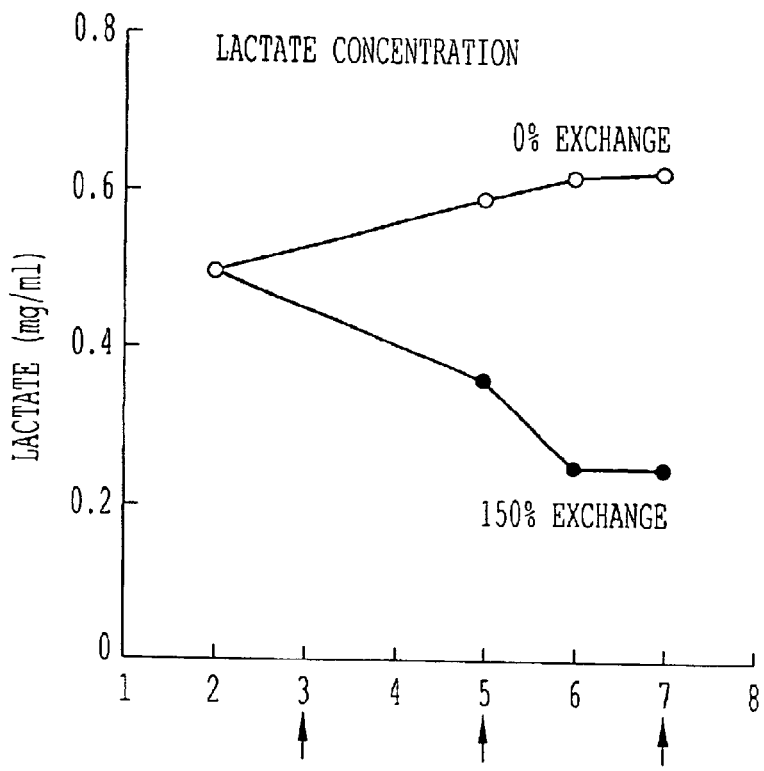
FIG. 3 shows (A) the lactate concentration during a dendritic cell culture according to the present invention (150% exchange) and in a static culture (0% medium exchange) at intermediate inoculum density, and (B) the mixed leucocyte response (MLR) of the isolated dendritic cells.
Figure 3B:
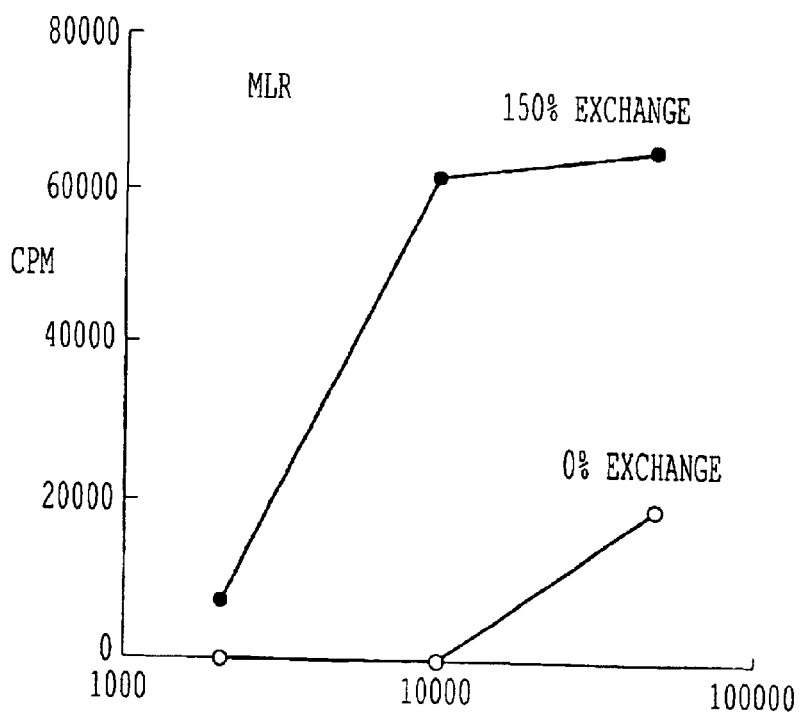
Figure 4A:
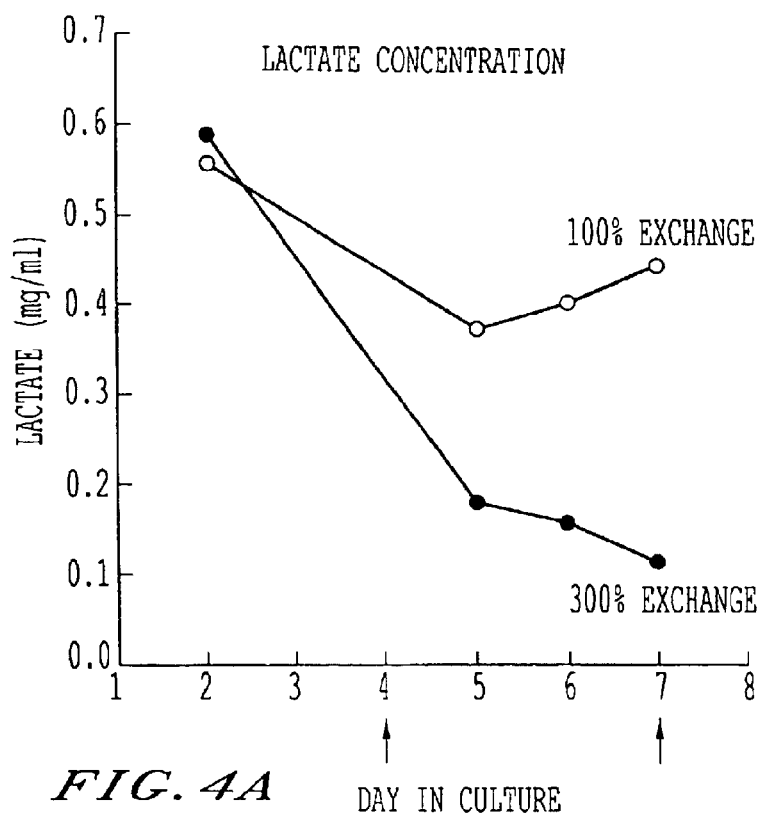
FIG. 4 shows (A) the lactate concentration during a dendritic cell culture according to the present invention at 100% exchange and 300% medium exchange at high inoculum density, and (B) the mixed leucocyte response (MLR) of the isolated dendritic cells.
Figure 4B:
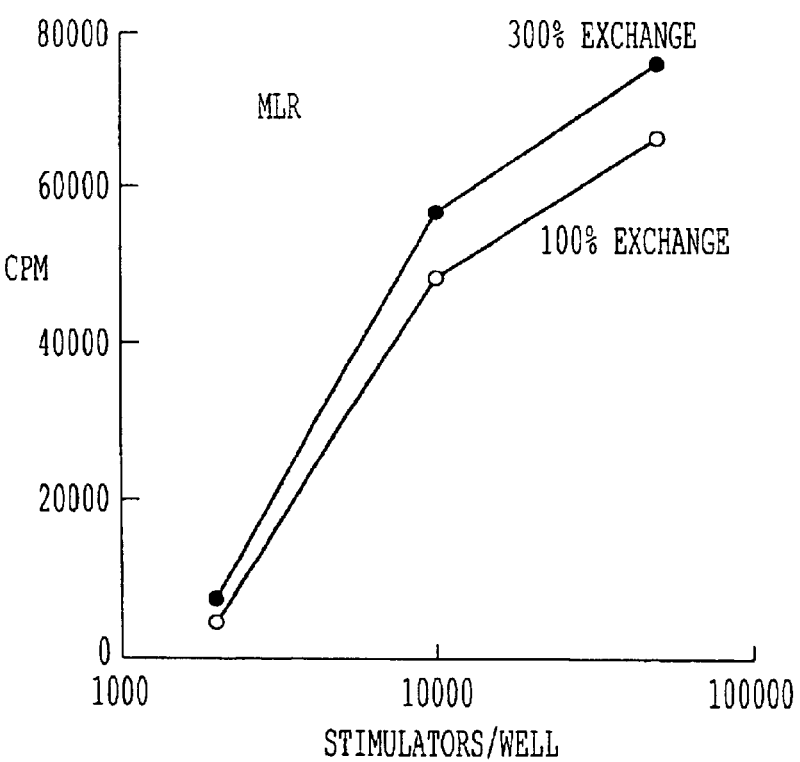

Results obtained with such small-scale cultures are shown in FIGS. 2–4. The cultures represented in FIG. 2, 3, and 4 were conducted at low, intermediate, and high inoculum density, respectively. Panel (A) of each Figure shows the lactate concentration as a function of time during the seven day culture period. Panel (B) of each Figure shows the mixed leucocyte response (MLR) observed with the harvested DCs. In these assays, the harvested DCs, which were derived from one individual, were contacted with the T-cells of another individual. The MLR response was determined by measuring the uptake of $^3$-H-thymidine in the stimulated T-cells (a measure of DNA synthesis in these T-cells) and is shown as "CPM" plotted against the number of harvested DCs in contact with the T-cells. The data in FIG. 2 shows the results obtained with 100% medium exchange and 0% medium exchange. In the medium-exchanged culture, 50% medium replacement was performed on day 4 and 7 (indicated by arrows in the FIG.). The data in FIG. 3 shows the results observed with 0% medium exchange and 150% medium exchange. In the medium-exchanged culture, 50% medium replacement was performed on day 3, 5, and 7 (indicated by arrows). FIG. 4 shows the results of culturing using 100% and 300% medium exchange. In the 100% exchange culture, the 50% of the medium was replaced at day 4 and 7 (indicated by the arrows in the Figure). For 300% medium exchange, 50% of the culture medium was replaced on day 2, 3, 4, 5, 6, and 7 (represented as a solid line in FIG. 4). These results show that increased rates of culture medium exchange produces harvested DCs with enhanced an enhanced ability to stimulate T-cells.

Example 4

Preliminary Optimization for Expansion of Chondrocytes

Figure 5:
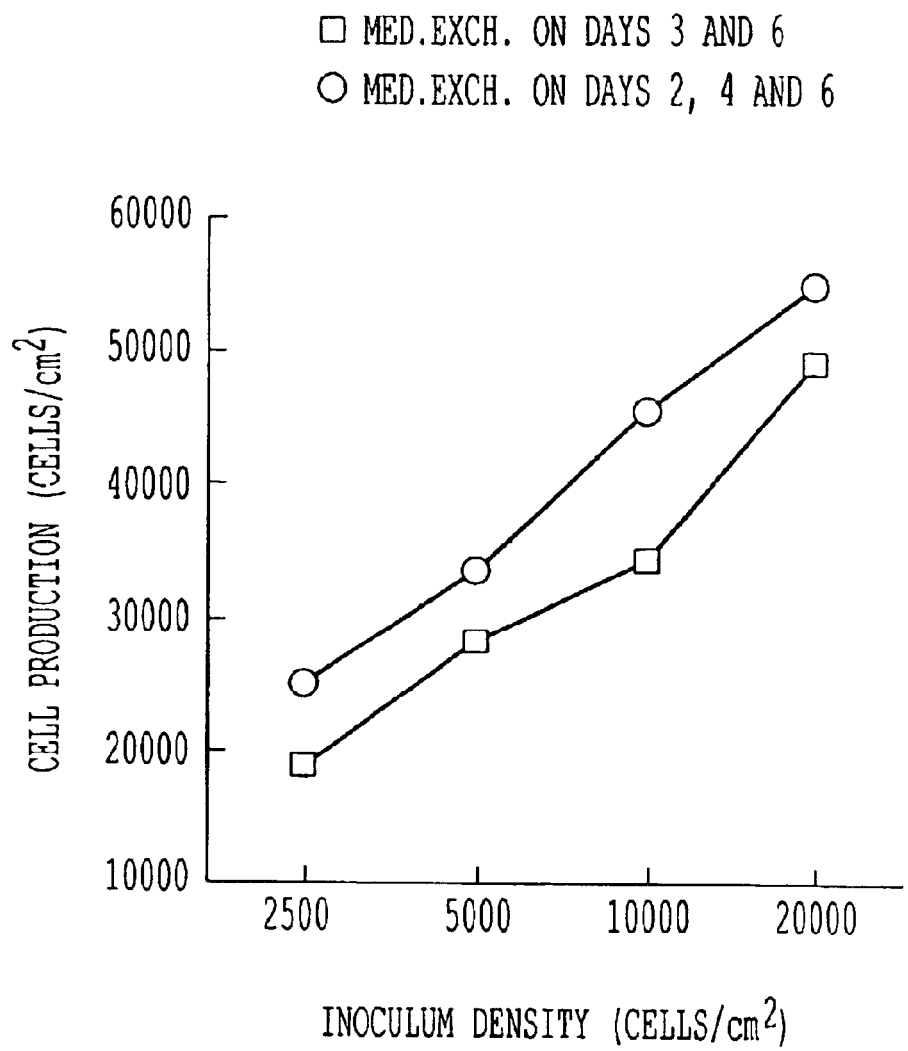
FIG. 5 shows the effect of medium exchange rate of canine chondrocyte production at different inoculum densitites.

To explore the benefits of medium exchange rate/perfusion with chondrocytes preliminary experiments were conducted with canine chondrocytes in a manual small scale system. Cells expanding in monolayer cultures were trypsinized and inoculated at different cell densities per cm$^2$ of the culture vessel (T-flask). The cultures were then expanded for several days at two rates of medium exchange (i) 50% medium exchange on day 3 and 5, and (ii) 50% medium exchange on days 2, 4, and 6. As is evident from FIG. 5, medium exchange rate can have a pronounced effect on the cell production. By increasing the medium exchange rate, a lower inoculum density can result in similar yield as two-fold higher inoculum density at lower medium exchange rate. The effects of perfusion rates becomes particular significant when the number of cells available for expansion is limited, resulting in more reliable generation of a target cell dose.

All publications and patent applications cited in this disclosure are incorporated herein by reference in their entirety.

Obviously, additional modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method for obtaining lineage-committed dendritic cells exhibiting enhanced biological function comprising culturing lineage committed dendritic cells ex vivo under physiologically acceptable liquid culture conditions, said conditions including replacement of the liquid culture medium at a rate of at least 25% daily replacement for more than one day and for a time sufficient to obtain lineage committed dendritic cells with enhanced biological function as compared with the biological function of the dendritic cells prior to the culturing.

2. The method of claim 1, wherein the biological function enhanced in the dendritic cells comprises at least one member selected from the group consisting of secretion of one or more substances, cell-cell communication, receptor expression on the cell surface, antigen presentation, antigen processing, ability to home in en vivo to sites for function, and the ability to stimulate T-cells.

3. The method of claim 1, wherein the liquid culture medium is replaced substantially continuously.

4. The method of claim 1, wherein the liquid culture medium is replaced periodically.

5. The method of claim 1, wherein the culture medium is replaced at a rate of at least 50% daily replacement for more than one day.

6. The method of claim 1, wherein the culture medium is replaced at a rate of iron 25 to 100% daily replacement for about $1\times10^4$ to about $1\times10^7$ cells/ml in culture for more than one day.

7. The method of claim 1, wherein the lineage committed dendritic cells are antigen-primed dendritic cells.

8. The method of claim 1, wherein the lineage committed dendritic cells are myeloid-derived dendritic cells.

9. The method of claim 1, wherein the lineage committed dendritic cells are lymphoid-derived dendritic cells.

10. A method for obtaining lineage-committed human dendritic cells exhibiting enhanced biological function comprising culturing lineage committed dendritic cells ex vivo under physiologically acceptable liquid culture conditions, said conditions including replacement of the liquid culture medium at a rate of at least 25% daily replacement for more than one day and for a time sufficient to obtain lineage committed dendritic cells with enhanced biological function as compared with the biological function of the human dendritic cells prior to the culturing.

11. The method of claim 10, wherein the biological function enhanced in the human dendritic cells comprises at least one member selected from the group consisting of secretion of substances, cell-cell communication, receptor expression on the cell surface, antigen presentation, antigen processing, ability to home in in vivo to sites for function, and the ability to stimulate T-cells.

12. The method of claim 10, wherein the liquid culture medium is replaced substantially continuously.

13. The method of claim 10, wherein the liquid culture medium is replaced periodically.

14. The method of claim 10, wherein the culture medium is replaced at a rate of at least 50% daily replacement for more than one day.

15. The method of claim 10, wherein the culture medium is replaced at aerate of from 25 to 100% daily replacement for about $1\times10^4$ to about $1\times10^7$ cells/ml or more than one day.

16. The method of claim 10, wherein the lineage-committed dendritic cells are antigen primed dendritic cells.

17. The method of claim 10, wherein the lineage-committed dendritic cells are myeloid derived dendritic cells.

18. The method of claim 10, wherein the lineage-committed dendritic cells are lymphoid-derived dendritic cells.

* * * * *